(12) United States Patent
Sano et al.

(10) Patent No.: US 6,392,125 B1
(45) Date of Patent: May 21, 2002

(54) METHOD FOR PRODUCING THE TRANSFORMANTS OF COFFEE PLANTS AND TRANSGENIC COFFEE PLANTS

(75) Inventors: Hiroshi Sano; Tomonobu Kusano, both of Ikoma (JP)

(73) Assignee: Nara Institute of Science and Technology, Ikoma (JP)

( * ) Notice: Subject to any disclaimer, the term of this patent is extended or adjusted under 35 U.S.C. 154(b) by 0 days.

(21) Appl. No.: 09/468,826

(22) Filed: Dec. 22, 1999

(30) Foreign Application Priority Data

Dec. 28, 1998 (JP) .......................................... 10-372647
Dec. 7, 1999 (JP) .......................................... 11-347812

(51) Int. Cl.⁷ ............................ A01H 5/00; A01H 4/00; C12N 5/04; C12N 15/82; C12N 15/84
(52) U.S. Cl. ..................... 800/294; 800/298; 800/300; 435/469; 435/418; 435/430.1; 435/320.1
(58) Field of Search ................................. 800/279, 294, 800/300, 301, 302, 298; 435/469, 410, 418, 419, 430.1, FOR 118, FOR 192, 209, 200, 320.1, 431

(56) References Cited

PUBLICATIONS

Prescott, A. et al., "Plant Transformation." 1998, Molecular Biomethods Handbook, pp. 251–269.*
Sugiyama, M. et al., "Transformation of Coffee with Agrobacterium Rhizogenes.", 1995, Colloq. Sci. Int. Café, vol. 2, pp. 853–859.*
Freire, A. V. et al., "Genetic Transformation of Coffee.", 1994, HortScience, vol. 29 (5), p. 454.*
Leroy, T. et al., "Introduction of genes of interest in agronomy into the coffee canephora species (Pierre) by transformation with agrobacterium Sp.", pp. 1–6.*
De Bondt, A. et al., "Agrobacterium–mediated transformation of apple (Malus x domestica Borkh.): an assessment of factors affecting gene transfer efficiency during early transformation steps." 1994, Plant Cell Reports, vol. 13, pp. 587–593.*
Lulsdorf, M. M. et al., "Optimizing the production of transformed pea (Pisum sativum L.) callus using disarmed Agrobacterium tumefaciens strains." 1991, Plant Cell Reports, vol. 9, pp. 479–483.*
Hatanaka, T. et al., "Transgenic plants of coffee Coffea canephora from embryogenic callus via Agrobacterium Tumefaciens–mediated transformation." 1999, Plant Cell Reports, vol. 19, pp. 106–110.*
Spiral et al., *C.R. Acad. Sci. Paris*, 316: 1–6 (1993).
Colloq. Sci. Int. Cafe 17 (1997) p. 439–446.
Antibiot Khimioter 35 [12] (1990) p. 24–26.
Simone S. Moesli Waldhauser et al, "Separation of the N–7–Methyltransferase, the key enzyme in caffeine biosynthesis", Phytochemistry, vol. 45., No. 7, pp. 1407–1414, 1997.

* cited by examiner

Primary Examiner—David T. Fox
Assistant Examiner—Anne Kubelik
(74) Attorney, Agent, or Firm—Oliff & Berridge, PLC

(57) ABSTRACT

A method of genetic improvement of coffee plants, using technique of molecular bleeding, is disclosed. The method provides a transformant of coffee plants produced from embryogenic calli, using Agrobacterium method.

5 Claims, 12 Drawing Sheets

(11 of 12 Drawing Sheet(s) Filed in Color)

(A) GUS (B) HPT

FIG. 17
FIG. 18
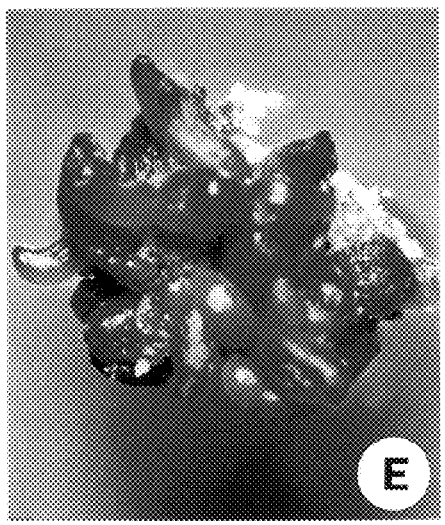
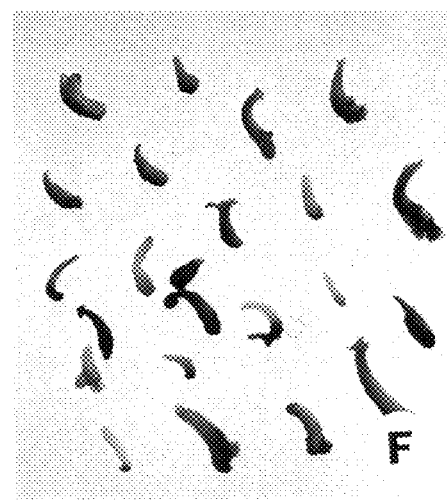

FIG. 21
FIG. 22
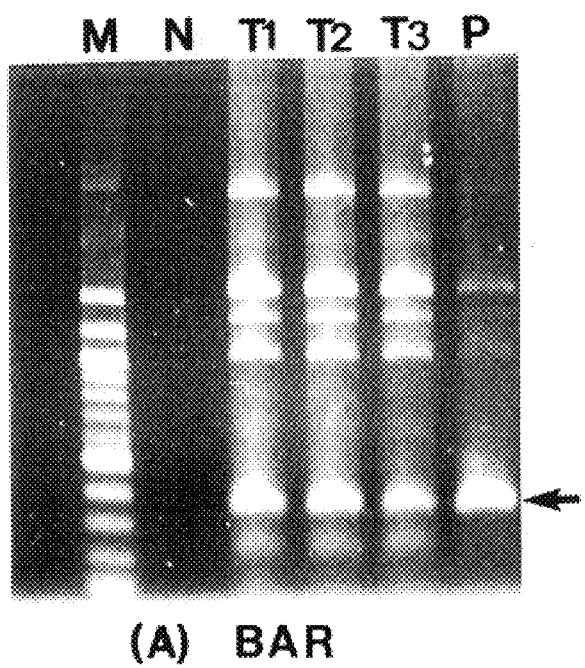
(A) BAR
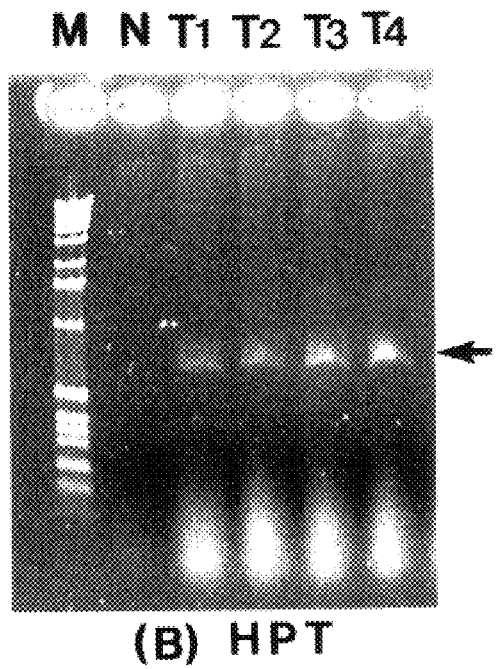
(B) HPT

SEQUENCE LISTING

<160> NUMBER OF SEQ ID NOS: 6

<210> SEQ ID NO 1
<211> LENGTH: 19
<212> TYPE: DNA
<213> ORGANISM: primer used for amplifying GUS gene

<400> SEQUENCE: 1
aattgatcag cgttggtgg                                                19

<210> SEQ ID NO 2
<211> LENGTH: 20
<212> TYPE: DNA
<213> ORGANISM: primer used for amplifying GUS gene

<400> SEQUENCE: 2
acgcgtggtt acagtcttgc                                               20

<210> SEQ ID NO 3
<211> LENGTH: 20
<212> TYPE: DNA
<213> ORGANISM: primer used for amplifying the HPT gene

<400> SEQUENCE: 3
gcgtgaccta ttgcatctcc                                               20

<210> SEQ ID NO 4
<211> LENGTH: 20
<212> TYPE: DNA
<213> ORGANISM: primer used for amplifying the HPT gene

<400> SEQUENCE: 4
ttctacacag ccatcggtcc                                               20

<210> SEQ ID NO 5
<211> LENGTH: 21
<212> TYPE: DNA
<213> ORGANISM: primer used for amplifying the bar gene

<400> SEQUENCE: 5
atgagcccag aacgacgccc g                                             21

<210> SEQ ID NO 6
<211> LENGTH: 22
<212> TYPE: DNA
<213> ORGANISM: primer used for amplifying the bar gene

<400> SEQUENCE: 6
gctcttgaag ccctgtgcct cc                                            22

METHOD FOR PRODUCING THE TRANSFORMANTS OF COFFEE PLANTS AND TRANSGENIC COFFEE PLANTS

BACKGROUND OF THE INVENTION

1. Field of the Invention

This invention relates to a method for producing the stable transformants of coffee plants.

2. Description of Related Art

Coffee is a commercially important woody shrub planted in a large scale for harvesting its beans. Among more than 80 species, the most economically important are *Coffee arabica* (2n-44) and *C. canephora* (2n-22). In *C. arabica*, genetic diversity is limited by conventional breeding because of its self-pollination characteristic, and the plants are highly sensitive to pests and diseases. *C. canephora*, used for instant coffee powder products, is a cross-pollinated specie but has low production quality. Conventional breeding of coffee is difficult because of the long duration of cultivation to set seeds. Molecular breeding, therefore, is a desirable technique for the genetic improvement of coffee species, although production of transgenic coffee plants via gene transformation has generally been considered problematic.

Plant regeneration via in vitro tissue culture is a basic system for achieving genetic transformation, and there have been many reports involving somatic embryogenesis in coffee plants (Staritsky, 1970; Hatanaka et al. 1991; Menéndez-Yuffá and García, 1996). However, data for genetic transformation of coffee are limited. Barton et al. (1991) obtained transformants from electroporated protoplasts of *C. arabica*, but the cultured protoplasts did not develop into whole plants. Spiral et al. (1993) reported the transformation of coffee (*C. canephora*) by co-cultivation of Agrobacterium rhizogenes with microcut-somatic embryos. However, the efficiency of transformation was very low. Van Boxtel et al. (1995) reported only transient expression of GUS genes on the surfaces of coffee leaf tissues following biolistic delivery.

SUMMARY OF THE INVENTION

Agrobacterium tumefaciens-mediated transformation is considered to be best for plant transformation because of the availability of vectors. Despite such advantage, no report has been presented of successful coffee transformation using Agrobacterium tumefaciens strains, except for GUS positive transgenic callus induction at a low frequency reported from Ocampo and Manzanera (1991).

This invention provides the successful genetic transformation of *Coffea canephora* using Agrobacterium tumefaciens EHA101 harboring pIG121-Hm from embryogenic calli.

Embryogenic calli were induced from leaf explants of *Coffea canephora* on McCown's woody plant medium (WPM) supplemented with 5 $\mu$M $N^6$-[2-isopentenyl]-adenosine (2-iP). These calli were co-cultured with Agrobacterium tumefaciens EHA101 harboring pIG121-Hm, containing β-glucuronidase (GUS)-, hygromycin phosphotransferase (HPT)- and neomycin phosphotransferase II (NPT II) genes. Selection of putative transgenic callus was performed by gradual increase in hygromycin concentrations (5, 50, 100 mg/l). The embryogenic calli surviving on a medium containing 100 mg/l hygromycin showed a strong GUS positive reaction with X-gluc solution. Somatic embryos were formed and germinated from these putative transgenic calli on WPM medium with 5 $\mu$M 2-iP. Regenerated small plantlets with shoots and roots were transferred to a medium containing both 100 mg/l hygromycin and 100 mg/l kanamycin for final selection of transgenic plants. The selected plantlets exhibited strong GUS activity in leaves and roots as indicated by a deep blue color. GUS and HPT genes were confirmed to be stably integrated into the genome of the coffee plants by the polymerase chain reaction (PCR).

Moreover, the inventors have succeeded in production of a transgenic plant of *Coffea arabica*, wherein phosphinothricin acetyl transferase (BAR) gene was incorporated to render resistance against herbicide. Commercially, *Coffea arabica* is more valuable than *Coffea canephora*. Embryogenic calli derived from *Coffea arabica* were induced from leaf explants of coffee on Murashige and Skoog (MS) medium supplemented with 10 $\mu$M $N^6$-[2-isopentenyl]-adenosine (2-iP). These calli were co-cultured with Agrobacterium tumefaciens EHA101 harboring pSMBuba, containing herbicide resistant BAR gene and hygromycin phosphotransferase (HPT) gene. Selection of putative transgenic callus was performed by gradual increase in hygromycin concentrations (25, 50 mg/l). The embryogenic calli maintained on MS medium with 50 mg/l hygromycin and 10 $\mu$M 2-iP. Prolonged culture of embryogenic callus induced somatic embryos. Germination of somatic embryos strongly enhanced by $GA_3$ treatment and developed into transgenic plantlets after 2 months of culture. Transgenic embryogenic callus, somatic embryos and small plantlets were tolerant to 2 mg/l Bialaphos. Whereas non-transformed ones were dead after 1 month. Prescence of HPT and BAR genes in those transgenic plantlets was confirmed by the genomic PCR and Northern assays.

This invention provides a method to incorporate an exogenous gene using Agrobacterium tumefaciens mediated method. Embryogenic calli were induced from leaf explants of coffee plants. The embryogenic calli thus obtained were infected by Agrobacterium tumefaciens, harboring a plasmid containing an exogenous gene to be incorporated and hygromycin phosphotransferase (HPT) gene. Putative transformed calli were selected using the hygromycin resistance as an indicator. And then somatic embryos were induced from the putative transformed calli. Transformed plantlets can be regenerated from the somatic embryos thus obtained.

Various species of coffee plants can be transformed using the method of this invention. The coffee plant species may preferably be cultivative coffee species such as *Coffea arabica, Coffea canephora, Coffea liberica* and *Coffea dewevrei*.

Theoretically, any exogenous gene can be incorporated into coffee plants by the method of this invention. The exogenous genes to be incorporated may preferably be caffeine synthetase gene, herbicide resistance gene such as phosphinothricin acetyl transferase (BAR) gene, insect injury resistance gene such as Bacillus thuringiensis gene, and disease resistance gene such as chitinase gene and glucanase gene.

Other and further objects, features and advantages of the invention will appear more fully from the following descriptions. It is to be understood that, examples mentioned above and description of detailed embodiments are not to be intended to limit the range of this invention.

BRIEF DESCRIPTION OF THE DRAWINGS

The file of this patent contains at least one drawing executed in color. Copies of this patent, with color drawings, will be provided by the Patent and Trademark Office upon request and payment of the necessary fee.

FIG. 17 shows somatic embryo on ½ MS medium containing $GA_3$.

FIG. 18 shows browned small plantlets cultured on ½ MS medium containing 2 mg/l bialaphos.

FIG. 21 shows detection of BAR gene using PCR, wherein the lanes T1 to T4 indicate results of transformed samples and the lane N indicates that of non-transformed sample.

FIG. 22 shows detection of HPT gene using PCR, wherein the lanes T1 to T4 indicate results of transformed samples and the lane N indicates that of non-transformed sample.

DETAILED DESCRIPTION OF EMBODIMENTS

EMBODIMENT 1

Figure 1:
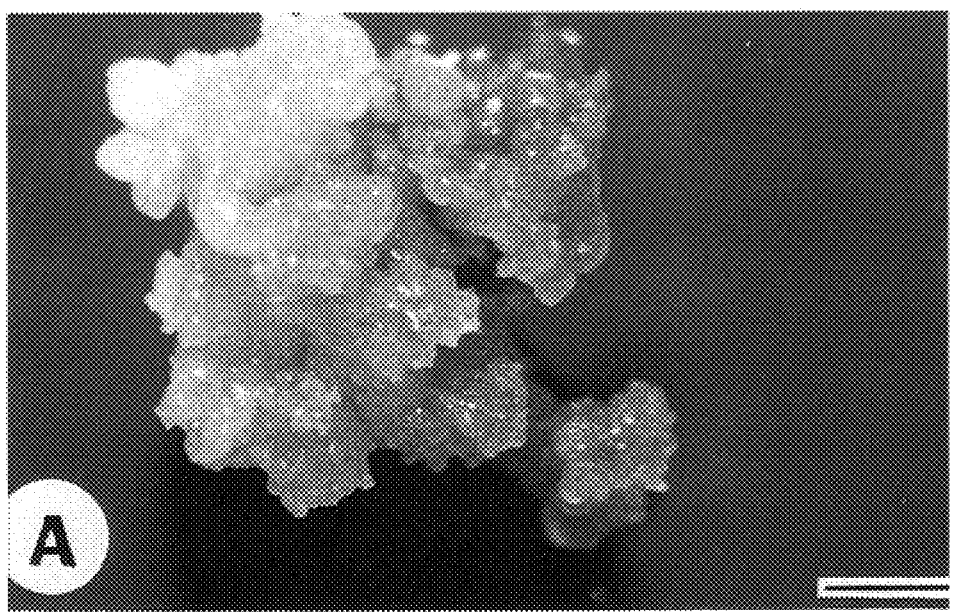
FIG. 1 shows embryogenic coffee callus surviving on WPM medium containing 100 mg/l hygromycin after co-cultivation with Agrobacterium tumefaciens EHA 101.

Production of a Transformant of *Coffea canephora*

Induction of Embryogenic Calli

Leaf explants of coffee (*Coffea canephora*) were prepared from leaves of greenhouse-grown trees, according to the method previously described (Hatanaka et al. 1991). The leaf explants were cultured on woody plant agar (0.9%) media (WPM) which consisted of McCown's woody plant salt mixture (Lloyd and McCown, 1981), Gamborg's $B_5$ (Gamborg et al. 1968) vitamins, 3% sucrose and 5 μM $N^6$-[2-isopentenyl]-adenosine (2-iP). The medium was adjusted to pH 5.7 before autoclaving at 120° C. for 15 min. The culture room was maintained at 25° C. with 16-h light illumination of 24 μmol $m^{-2}s^{-1}$ (white fluorescent tubes).

Agrobacterium Transformation

After 4 months of the above culture, embryogenic calli induced from the leaf explants were transferred to callus proliferation medium (CM) which consisted of MS salts (Murashige and Skoog, 1962), 0.25% Gellan Gum, $B_5$ vitamin, 3% sucrose and 10 μM 2,4-dichlorophenoxyacetic acid (2,4-D). The CM medium was also adjusted to pH 5.7 before autoclaving at 120° C. for 15 min. Agrobacterium tumefaciens EHA101 harboring pIG121-Hm containing β-glucuronidase (GUS)-, hygromycin phosphotransferase (HPT)- and neomycin phosphotransferase II (NPT II) genes in the T-DNA region of the plasmid was used for the transformation. Freshly subcultured embryogenic calli (3 days after culture) were co-cultivated in bacterial suspension (absorbance of 0.6 at 600 nm) for 30 min at 25° C. in WPM liquid medium containing 5 μM 2-iP and 50 mg/l acetosyringone, then these calli were transferred to WPM agar medium containing 50 mg/l acetosyringone, 3% sucrose and 5 μM 2-iP at 25° C. in the dark for four days. To eliminate bacteria, the calli were washed 5 times with sterilized water, followed by water containing 300 mg/l cefotaxime once. Thereafter the embryogenic calli were cultured on WPM agar medium containing 300 mg/l cefotaxime, 5 mg/l hygromycin, and 5 μM 2-iP, and subcultured on the same medium at 2 week intervals. After 2 months of culture, embryogenic calli were transferred to fresh medium with an increased concentration of hygromycin (50 mg/l). After 2 months of culture, each line of embryogenic callus was maintained by transferring to fresh WPM agar medium containing 5 μM 2-iP and 100 mg/l hygromycin.

Somatic Embryogenesis and Plant Regeneration

After selection at the concentration of 100 mg/l hygromycin, survived embryogenic calli were transferred to WPM medium containing 5 μM 2-iP in 10×2 cm plastic Petri dishes. Partially germinated embryos (about 1–2 cm in length) were transferred to phytohormone-free WPM agar medium containing both 100 mg/l hygromycin and 100 mg/l kanamycin for final selection of transgenic plantlets. After selection, they were cultured on WPM agar medium without growth regulators to support continued growth in 300 ml culture bottles. Plantlets with both shoots and roots were transferred to plastic pots containing soil and peat moss (1:1 v/v) in a greenhouse.

Histochemical GUS Assay

Histochemical assays of GUS were performed for hygromycin-resistant embryogenic calli, somatic embryos, and leaves and roots of plantlets, according to the method of Van Boxtel et al. (1995). For staining, the materials were incubated in 5-bromo-4-chloro-3-indolyl-β-D-glucuronide (X-gluc) solution with a composition modified to 50 mM $Na_2HPO_4$, 10 mM $Na_2EDTA$, 0.3% Triton X-100, 0.5 mM $K_3Fe(CN)_6$, 0.5 mM $K_4Fe(CN)_6$, and antioxidants (0.5% caffeine, 1% PVP and 1% sodium ascorbate). After 16 hours at 37° C., these explants were immersed in 99.5% ethanol for chlorophyll bleaching and observed under a dissecting microscope.

Agrobacterium-mediated Transformation and Somatic Embryogenesis

Figure 2:
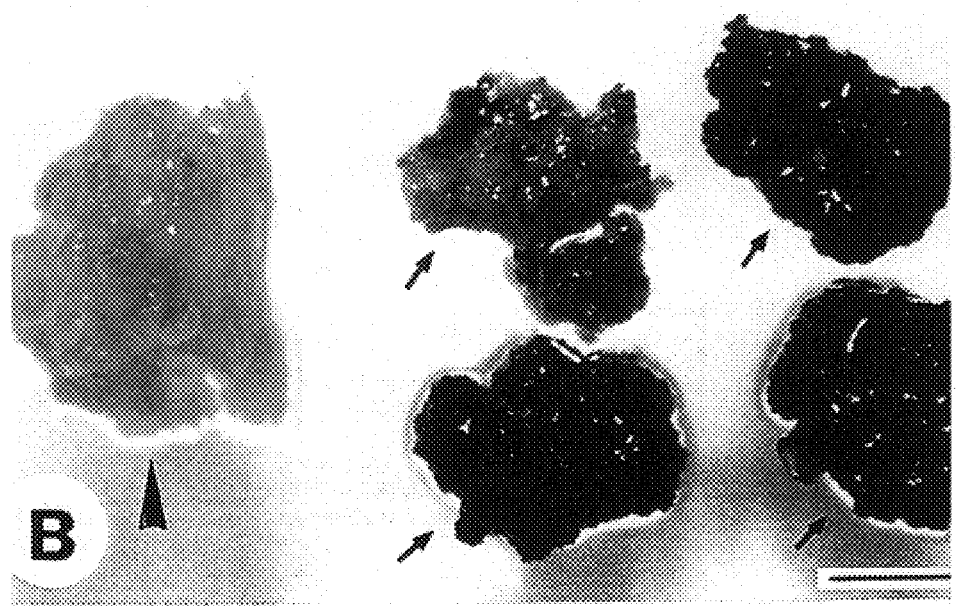
FIG. 2 shows GUS activity staining of transformed or non-transformed embryogenic calli.
Figure 10:
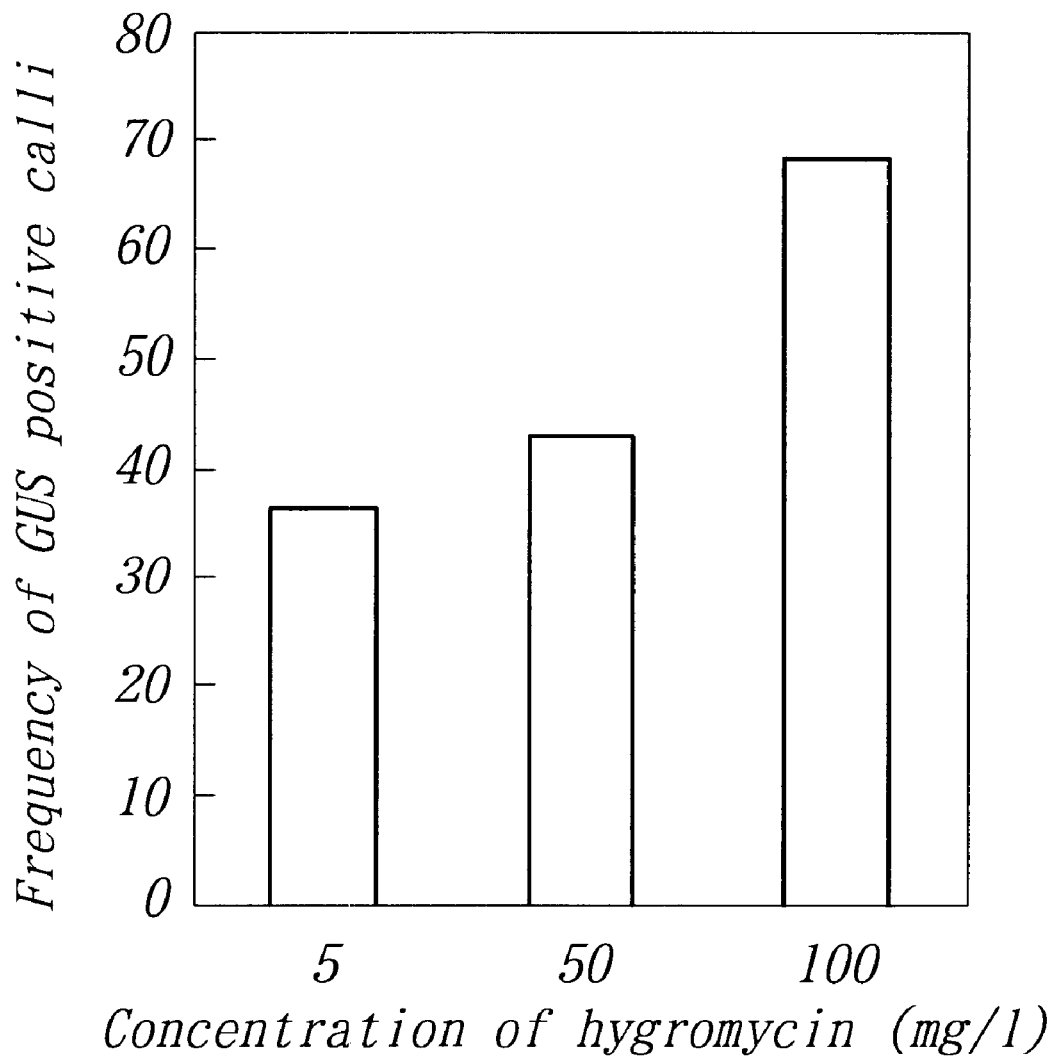
FIG. 10 shows frequency of GUS positive calli from survived embryogenic calli of coffee on selection media.

Friable and yellow (FIG. 1) embryogenic calli were obtained from leaf explants of coffee (*Coffea canephora*) after 4 months of culture on WPM agar medium with 5 μM 2-iP. Embryogenic calli were co-cultivated with Agrobacterium tumefaciens EHA101, a super-virulent line for rice transformation (Hiei et al. 1994; Yokoi et al. 1996), in WPM medium containing 50 mg/l 2 acetosyringone and 5 μM 2-iP for 30 min. After washing in sterilized water, embryogenic calli were transferred to CM solid medium containing 50 mg/l acetosyringone in the dark for 4 days. It has been reported that acetosyringone treatment is highly effective for increasing the transformation efficiency (James et al. 1993). To eliminate remnant bacteria, embryogenic calli were transferred to WPM medium containing 300 mg/l cefotaxime, 5 mg/l hygromycin and 5 μM 2-ip. After 2 months of culture, about 90% of the calli (267 out of 298 calli) survived on WPM medium with 5 mg/l hygromycin, and 96 calli (36.0%) demonstrated GUS positive blue spots after immersion in X-gluc solution (FIG. 10). Thereafter, the survived calli were transferred to the same medium containing 50 mg/l hygromycin. After 2 months of culture, 81 (43.3%) out of 187 calli that survived on medium with 50 mg/l hygromycin had blue spots by X-gluc reaction (FIG. 10). These 187 calli were transferred to WPM medium containing 100 mg/l hygromycin and 131 calli (70.1%) continued to proliferate even after 2 months of incubation. When the hygromycin resistant embryogenic calli were reacted with X-gluc solution, 90 calli (68.7%) showed a strong GUS positive reaction (FIG. 2, arrows, FIG. 10). However, embryogenic calli without co-cultivation did not show any GUS activity (FIG. 2, arrowhead).

Figure 3:
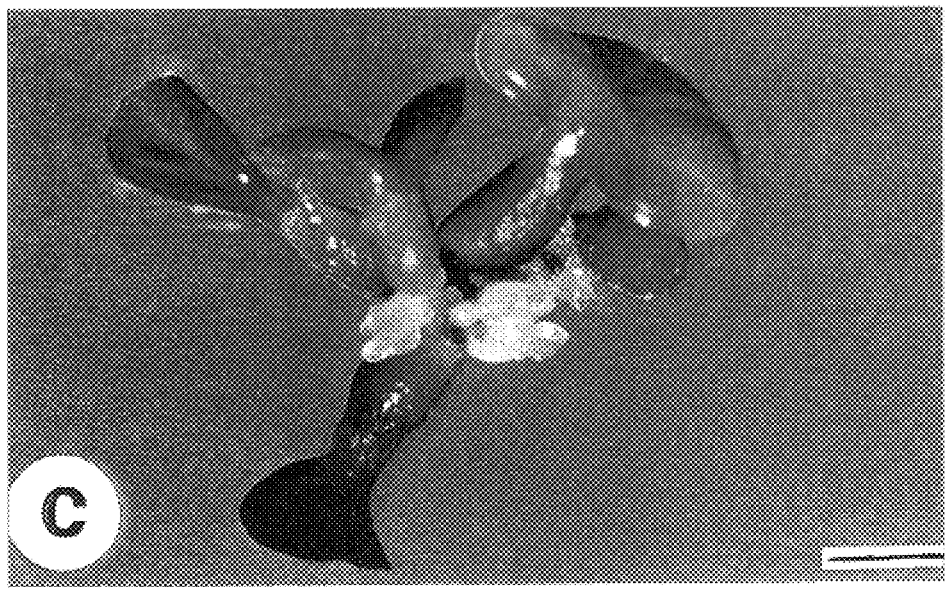
FIG. 3 shows formation of somatic embryo, derived from transformed embryogenic calli.
Figure 4:
FIG. 4 shows GUS activity staining of somatic embryos, derived from transformed or non-transformed embryogenic calli.

After selection of survived embryogenic calli in the presence of 100 mg/l hygromycin, embryogenic calli were transferred to WPM medium with 5 μM 2-iP. Numerous somatic embryos were formed from the putative transgenic calli after 2 months of culture (FIG. 3). The X-gluc reaction revealed that somatic embryos (FIG. 4, arrows) were formed from hygromycin resistant embryogenic calli to be positive. Somatic embryos from non-transformed embryogenic calli (FIG. 4, arrowhead) were stained negatively except for intrinsic reaction with pale blue color. It had been reported that intrinsic GUS-like activity was observed in immature and mature somatic embryos of coffee (Van Boxtel et al. 1995).

A Production of Transgenic Plantlets

Figure 5:
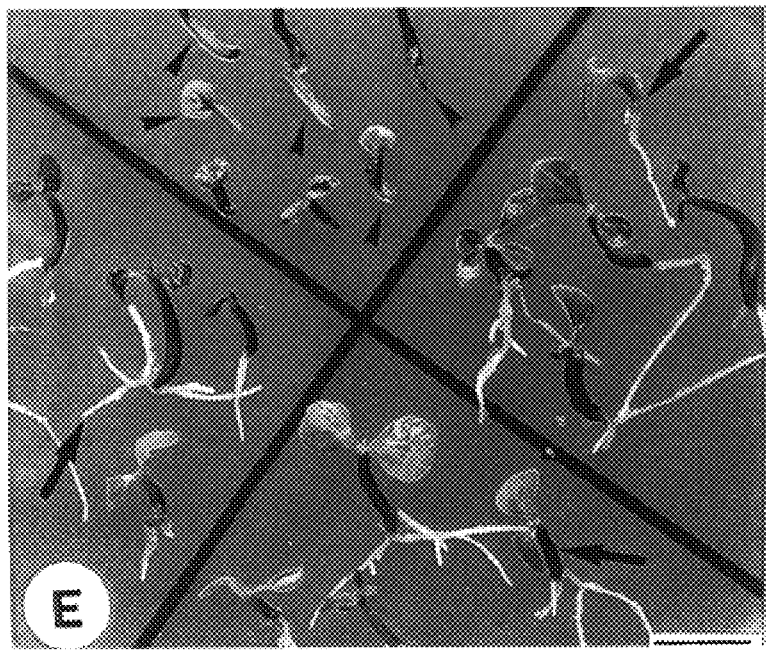
FIG. 5 shows small plantlets cultured on WPM medium containing both 100 mg/l hygromycin and 100 mg/l kanamycin.
Figure 6:
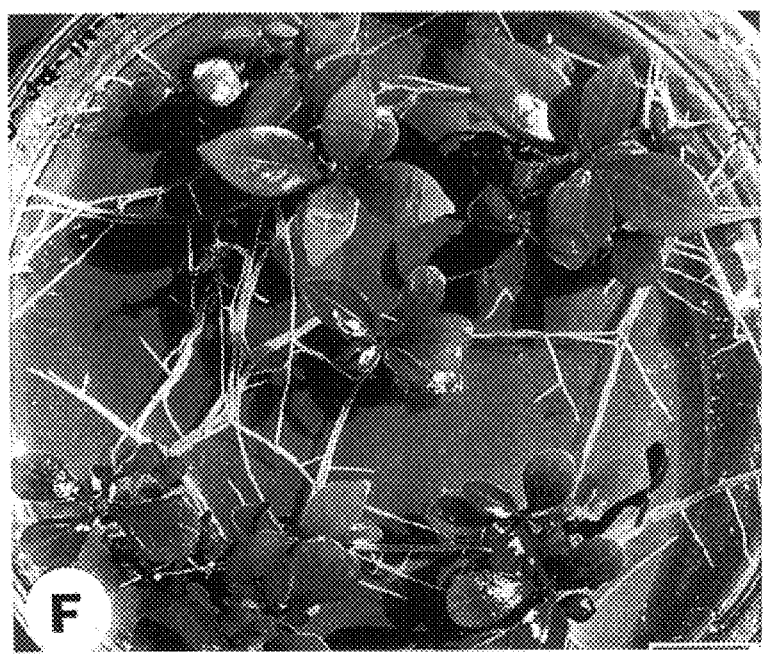
FIG. 6 shows hygromycin and kanamycin resistant putative transgenic plantlets after transfer to WPM medium supplemented with 3% sucrose.
Figure 9:
FIG. 9 shows a transgenic coffee plantlets after transfer to soil.

Somatic embryos germinated and regenerated to small plantlets with shoots and roots after transferring to WPM medium lacking growth regulators. To check finally the transgenic plantlets, the small plantlets (1–2 cm in length) were transferred to WPM medium containing both 100 mg/l hygromycin and 100 mg/l kanamycin. In this medium, non-transformed plantlets did not grow at all and rapidly browned (FIG. 5, arrowheads), whereas transformed plantlets grew very well (FIG. 5, arrows). Especially, the roots thrived without showing any growth suppression and browning. Eighty seven % of plantlets survived on this medium. After transfer to a medium without growth regulators in Petri dishes (FIG. 6) or 300 ml culture bottles, these plantlets grew to about 7 cm in height with about 6–10 leaves and formed well-developed roots after 3–5 months of culture. Transgenic plantlets were transferred to a mixture of autoclaved soil in a greenhouse. Most of the plants survived without wilting and the loss of their green color (FIG. 9).

Figure 7:
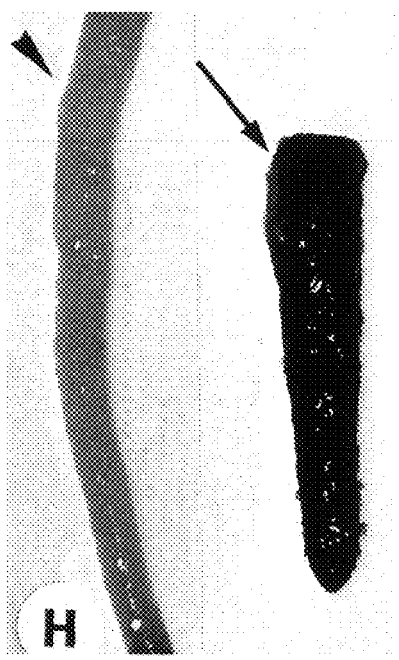
FIG. 7 shows GUS activity staining of leaves, derived from a non-transformed or transformed coffee plant.
Figure 8:
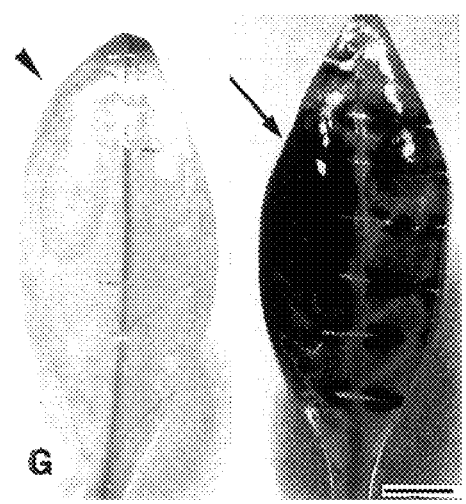
FIG. 8 shows GUS activity staining of roots, derived from a non-transformed or transformed coffee plant.

The leaves (FIG. 7, arrow) and roots (FIG. 8, arrow) of the putative transgenic plantlets demonstrated a deep blue color on reaction with X-gluc. Explants from non-transformed plantlets (FIGS. 7–8, arrowheads) did not react with X-gluc. While leaf tissues in the transformed case were not always stained by X-gluc, the roots always showed a strong GUS positive reaction. Furthermore, surgical wounding on leaf surfaces increased their positivity (FIG. 7), suggesting a blocking effect of the well-developed cuticle of the coffee leaf.

PCR Analysis of GUS and HPT Genes

DNA extraction from leaves of coffee plantlets having positive GUS activity was carried out according to the described procedure (Kikuchi et al. 1998) using the modified (addition of 3% 2-mercaptoethanol in solution 1) benzyl chloride method (ISOPLANT kit, Wako Co.). The primers [SEQ ID NOS.: 1–4] used for amplifying the GUS gene were 5'-AATTGATCAGCGTTGGTGG-3' and 5'-ACGCGTGGTTACAGTCTTGC-3' and those for the HPT gene were 5'-GCGTGACCTATTGCATCTCC-3' and 5'-TTCTACACAGCCATCGGTCC-3'. The reaction mixture for PCR was incubated in a DNA thermal cycler (Perkin Elmer Cetus, 9700) under the following conditions: 96° C. for 5 min, followed by 30 cycles of 94° C. for 30 sec, 58° C. for 30 sec, and 72° C. for 2 min with a final 5 min extension at 72° C.

Figure 11:
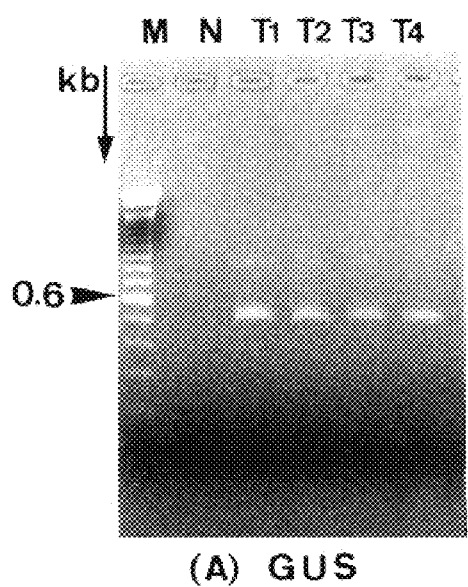
FIG. 11 shows detection of GUS gene using PCR, wherein the lanes T1 to T4 indicate results of transformed samples and the lane N indicates that of non-transformed sample.
Figure 12:
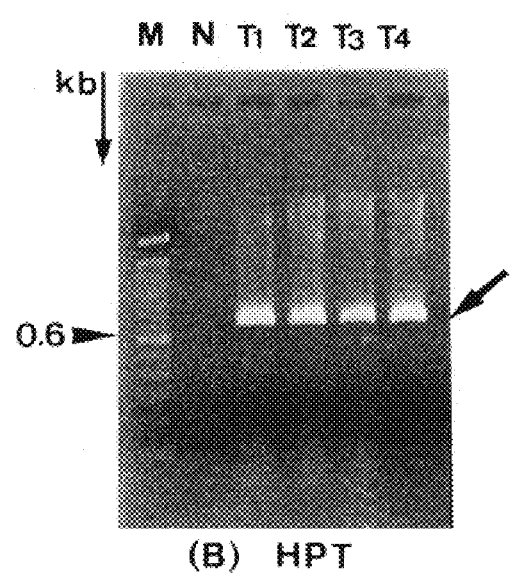
FIG. 12 shows detection of HPT gene using PCR, wherein the lanes T1 to T4 indicate results of transformed samples and lane N indicates that of non-transformed sample.

Examination of the leaves of GUS positive transgenic plantlets (T) by PCR revealed amplified fragments coinciding with the GUS (515 bp band in FIG. 11) and HPR (713 bp band in FIG. 12) genes. In non-transformed plantlets (N), neither GUS nor HPR genes were detectable.

EMBODIMENT 2

Production of a Tranformant of *Coffea arabica* with Herbicide Resistance

Induction of Embryogenic Calli

Leaf explants of coffee (*Coffea arabica*) were prepared from leaves of greenhouse-grown trees, according to the method described previously (Hatanaka et al. 1991). Leaf explants were cultured on Murashige and Skoog agar (0.9%) medium (Murashige and Skoog, 1962) containing Gamborg's $B_5$ (Gamborg et al. 1968) vitamins, 3% sucrose and 10 μM $N^6$-[2-isopentenyl]-adenosine (2-iP). The medium was adjusted to pH 5.7 before autoclaving at 120° C. for 15 min. The culture room was maintained at 25° C. with 16-h light illumination of 24 μmol $m^{-2}s^{-1}$ (white fluorescent tubes).

Agrobacterium Transformation

After selection of embryogenic callus, these calli were serially subcultured by two-week intervals onto MS medium supplemented with 0.9% agar, $B_5$ vitamin, 3% sucrose and 10 μM 2-iP to induce friably embryogenic callus. Agrobacterium tumefaciens EHA101 harboring pSMBuba containing BAR and hygromycin phosphotransferase (HPT) genes in the T-DNA region of the plasmid was used for the transformation. Freshly subcultured embryogenic calli (3 days after culture) were co-cultivated in bacterial suspension (absorbance of 0.6 at 600 nm) for 30 min at 25° C. in MS liquid medium containing 10 μM 2-iP and 10 mg/l acetosyringone, then these calli were transferred to MS agar medium containing 10 mg/l acetosyringone, 3% sucrose and 10 μM 2-iP at 25° C. in the dark for four days. To eliminate bacteria, the calli were washed for 5 times with sterilized water, followed by water containing 300 mg/l cefotaxime once. Thereafter the embryogenic calli were cultured on MS agar medium containing 300 mg/l cefotaxime and 10 μM 2-iP, and subcultured on the same medium at 2 week intervals. After 2 months of culture, embryogenic calli were transferred to fresh MS medium containing hygromycin (25 mg/l) for one month. Thereafter, each line of embryogenic callus was maintained by transferring to fresh MS agar medium containing 10 μM 2-iP and 50 mg/l hygromycin by three weeks of culture cycle.

Somatic Embryogenesis and Plant Regeneration

To induce somatic embryos, embryogenic callus maintained on MS medium with 10 μM 2-iP was transferred to MS medium with 3 μM 2-iP. Somatic embryos developed spontaneously from embryogenic callus. After selection of somatic embryos, they were cultured on ½ MS agar medium with 10 μM GA$_3$ to support germination. After 3 weeks of culture, small plantlets were transferred to ½ MS agar medium in 300 ml Erlenmeyer flasks to support the further growth.

Observation of Bialaphos Resistance

Hygromycin-resistant embryogenic calli, somatic embryos, and small plantlets survived on medium containing 50 mg/l hygromycin were transferred to ½ MS medium containing 2 mg/l bialaphos. After one month of culture, survival rate was examined.

PCR Analysis of BAR and HPT Genes

DNA extraction from small coffee plantlets resistant to hygromycine was carried out according to a described procedure (Kikuchi et al. 1998) using a modified (addition of 3% 2-mercaptoethanol in solution 1) benzyl chloride method (ISOPLANT kit, Wako Co.). The primers [SEQ ID NOS.: 5–6 and 3–4, respectively] used for amplifying the bar gene were 5'-ATGAGCCCAGAACGACGCCCG-3' (forward) and 5'-GCTCTTGAAGCCCTGTGCCTCC-3' (reverse), and those for the BPT gene were 5'-GCGTGACCTATTGCATCTCC-3' (forward) and 5'-TTCTACACAGCCATCGGTCC-3' (reverse). The reaction mixture for PCR was incubated in a DNA thermal cycler (Perkin Elmer Cetus, 9700) under the following conditions: 96° C. for 5 min, followed by 30 cycles of 94° C. for 30 sec, 58° C. for 30 sec, and 72° C. for 2 min with a final 5 min extension at 72° C.

Agrobacterium-mediated Transformation and Somatic Embryogenesis

Figure 13:
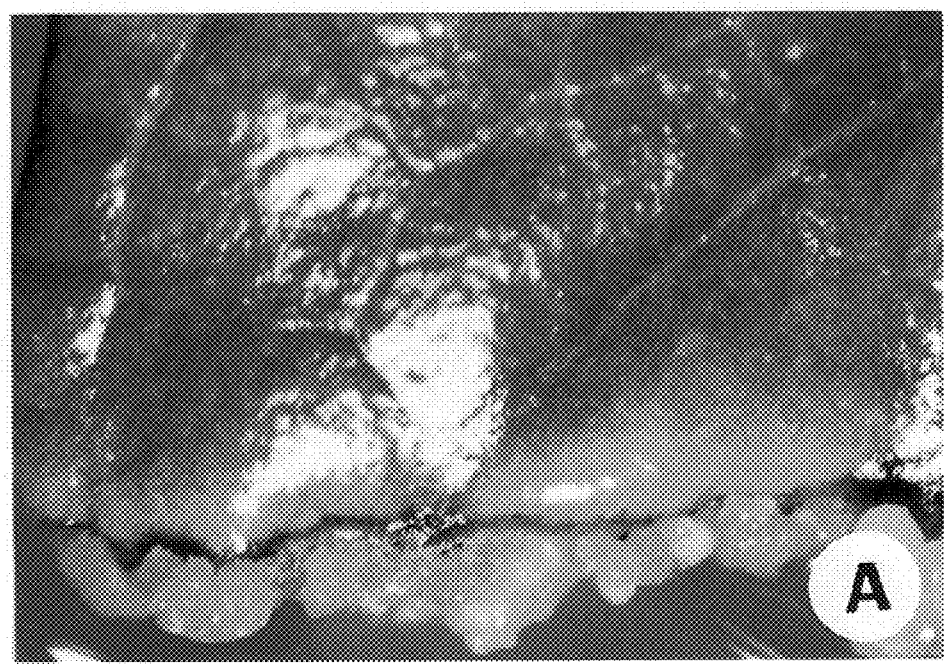
FIG. 13 shows embryogenic coffee callus derived from a leaf explant of *Coffea arabica*.
Figure 14:
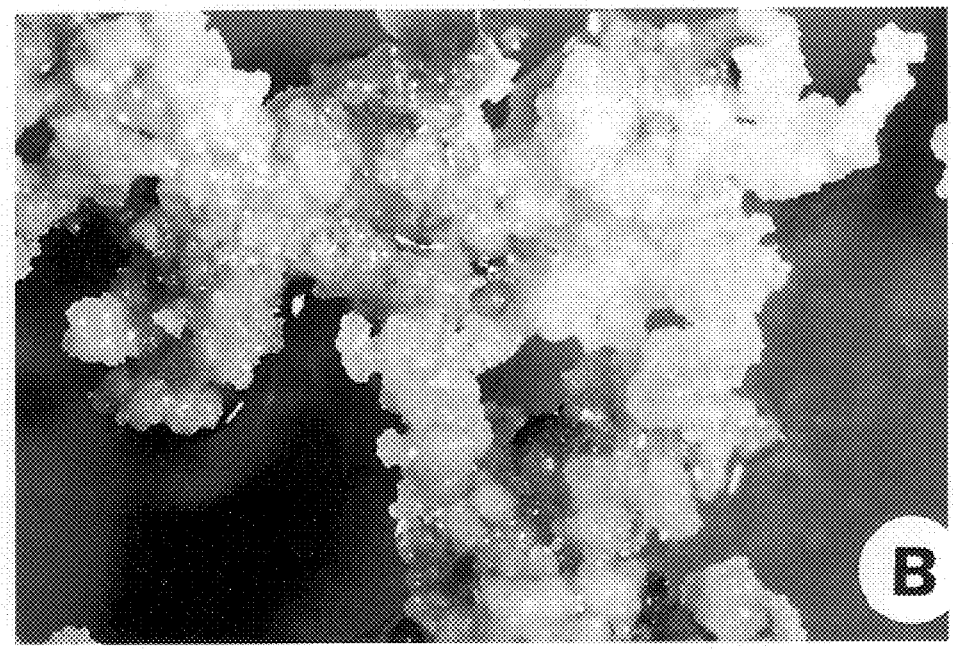
FIG. 14 shows embryogenic calli maintained in MS medium containing 2-iP.

Yellow (FIG. 13) embryogenic calli were obtained from excised margins of leaf explants of coffee (*Coffea arabica*) after 4 months of culture on MS agar medium with 10 μM 2-iP. These calli were selected and maintained on that medium by 3 weeks of subculture cycle (FIG. 14). Embryogenic calli were co-cultivated with Agrobacterium tumefaciens EHA101 in MS liquid medium containing 10 mg/l acetosyringone and 10 μM 2-iP and transferred to MS solid medium containing 10 mg/l acetosyringone and 10 μM 2-iP in the dark for 4 days. To eliminate remnant bacteria, the co-cultivated embryogenic calli were transferred to MS medium containing 300 mg/l cefotaxime and 10 μM 2-iP. After 2 months of culture, these calli were transferred to the same medium containing 25 mg/l hygromycin. After 2 months of culture, survived embryogenic calli were transferred to MS medium containing 50 mg/l hygromycin.

Figure 15:
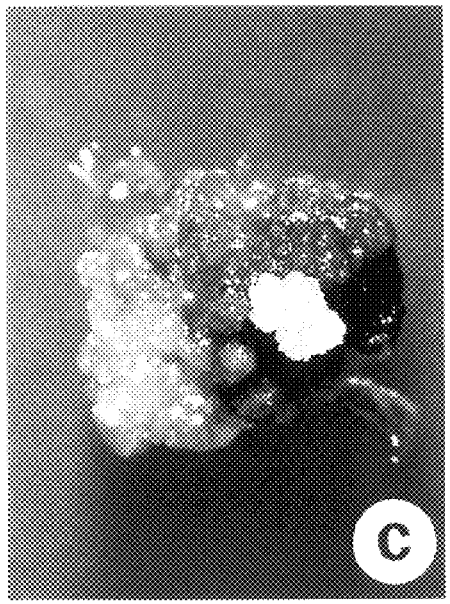
FIG. 15 shows survived embryogenic callus on the surface of browned non-transformed calli.

After selection of survived embryogenic calli (FIG. 15) in the presence of 50 mg/l hygromycin, these calli were transferred to MS agar medium containing 2 mg/l bialaphos. In 33% of embryogenic callus, proliferation and colour was not influenced by the bialaphos treatment. Whereas, in non-transformed callus, colour of callus rapidly turn to brown and did not proliferlated further after 2 weeks of culture.

Figure 16:
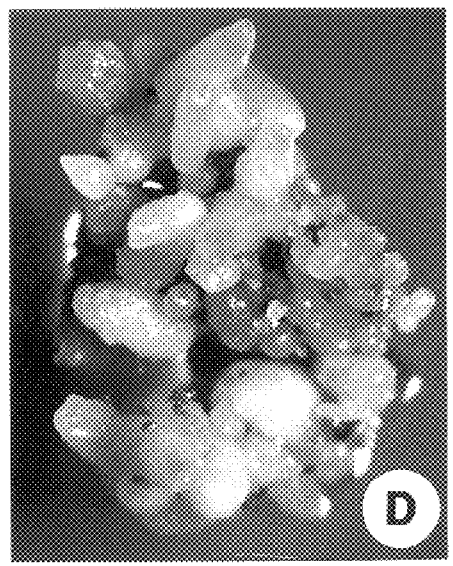
FIG. 16 shows somatic embryo formation from a transformed embryogenic callus of *Coffea arabica*.

To induce somatic embryos from embryogenic callus, embryogenic calli were transferred to MS medium containing 3 μM 2-iP. Prolonged culture of embryogenic callus stimulated somatic embryo formation from embryogenic cells. Over one month of subculture cycle was efficient for somatic embryo induction from callus. Numerous somatic embryos were formed from the putative transgenic calli after 2 months of culture (FIG. 16).

Germination of Transgenic Plantlets

Figure 19:
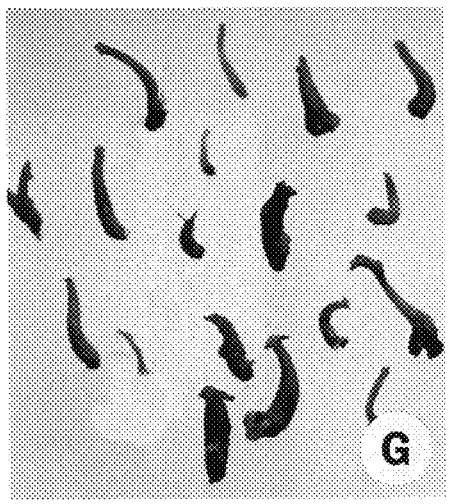
FIG. 19 shows the bialaphos resistance of transgenic small plantlets.
Figure 20:
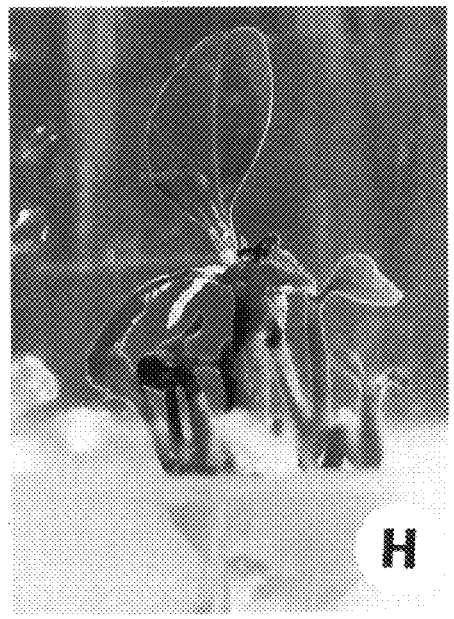
FIG. 20 shows a transgenic plantlets of *Coffea arabica* grew on ½ MS medium in flasks.

When somatic embryos were transferred to ½ MS medium containing 10 μM GA$_3$, germination frequency was strongly enhanced. All (100%) the embryos turn to green after 3 weeks of culture on GA$_3$ containing medium (FIG. 17). Whereas, only 37% of somatic embryos were in green colour after 3 weeks of culture on GA$_3$-free medium and germination speed of somatic embryos was very slow. Somatic embryo and small plantlets survived on 50 mg/l hygromycin also tolerant to the 2 mg/l bialaphos. Eighty three percent of somatic embryos and 92% of small plantlets were grew normally in 2 mg/l bilaphos without change of colour and growth ability (FIG. 19). While, in non-transformed somatic embryos and plantlets, most of them were browned and eventually dead after one to two months of culture (FIG. 18). These survived plantlets were transferred to ½ strength MS medium in 300 ml culture bottles for further growth (FIG. 20).

Examination of transgenic small plantlets (T) by genomic PCR revealed amplified fragments coinciding with the bar (362 bp band in FIG. 21) and HPT (713 bp band in FIG. 22) genes. In non-transformed plantlets (N), neither bar nor HPT genes were detectable (FIG. 21, FIG. 22).

References

Barton CR, Adams TL, Zarowitz MA (1991) Stable transformation of foreign DNA into *Coffea arabica* plants. In: 14$^e$meColloq Sci Int Café, ASIC, Paris, pp 460–464

Gamborg OL, Miller RA, Ojima K (1968) Plant cell cultures. (1) Nutrient requirements of suspension cultures of soybean root cells. Exp Cell Res 50: 151–158

Hatanaka T, Arakawa 0, Yasuda T, Uchida N, Yamaguchi T (1991) Effect of plant growth regulators on somatic embryogenesis in leaf cultures of Coffea canephora. Plant Cell Rep 10: 179–182

Hiei Y, Ohta S, Komari T, Kumashiro T (1994) Efficient transformation of rice (Oryza sativa L.) mediated by Agrobacterium and sequence analysis of the boundaries of the T-DNA. Plant J 6: 271–282

Hood EE, Halmer GL, Fraley RT, Chilton MD (1986) The hypervirulence of Agrobacterium tumefaciens A281 is encoded in a region pTIB0542 outside of T-DNA. J Bacteriol 168: 1291–1301

James DJ, Uratsu S, Cheng J, Negri P, Viss P, Dandekar AM (1993) Acetosyringone and osmoprotectants like betaine or proline synergistically enhance Agrobacterium-mediated transformation of apple. Plant Cell Rep 12: 559–563

Kikuchi K, Niwa Y, Yamaguchi T, Sunohara H, Hirano H-U, Umeda M (1998) A rapid and easy-handling procedure for isolation of DNA from rice, Arabidopsis and tobacco. Plant Biotechnology 15: 45–48

Lloyd G, McCown, B (1981) Commercially-feasible micropropagation of mountain laurel, Kalmia latiforia, by use of shoot tip culture. Comb Proc Int Plant Propagator's Soc. 30: 421–427

Menéndez-Yuffá A, García E de (1996) Coffea species (coffee) In: Bajai YPS (eds) Biotechnology in Agriculture and Forestry, Vol 35, Springer-Verlag, Berlin Heidelberg, pp 95–119

Murashige T, Skoog F (1962) A revised medium for rapid growth and bioassays with tobacco tissue. Physiol Plant 15: 473–497

Ocampo C, Manzanera L (1991) Advances in genetic manipulation of the coffee plant. In: 14$^e$meColloq Sci Int Café, ASIC, Paris, pp 378–382

Ohta S, Mita S, Hattori T, Nakamura K (1990) Construction and expression in tobacco of a β-glucuronidase (GUS) reporter gene containing an intron within the coding sequence. Plant Cell Physiol 31: 805–813

Spiral J, Thierry C, Paillard M, Pétiard V (1993) Obtention de plantules de Coffea canephora Pierre (Robusta) transformées par Agrobacterium rhizogenes. C R Acad Sci Paris Serff Sci Vie 316: 1–6

Staritsky G (1970) Embryoid formation in callus tissues of coffee. Acta Bot Neerl 19: 509–514

Van Boxtel J, Berthouly M, Carasco C, Dufour M, Eskes A (1995) Transient expression of β-glucuronidase following biolistic delivery of foreign DNA into coffee tissues. Plant Cell Rep 14: 748–752

Yokoi S, Toriyama K, Hinata K (1996) Protocol for production of transgenic rice plants mediated by Agrobacterium. Plant Tissue Culture Letters 13: 81–84

What is claimed is:

1. A method for producing a transformant of *Coffea arabica*, the method comprising the steps of: infecting an embryogenic callus of *Coffea arabica* with Agrobacterium tumefaciens EHA101 strain that comprises a vector containing an exogenous gene and a gene available for the selection of transformed embryonic callus to produce a transformed embryogenic callus in a medium containing $N^6$-[2-isopentenyl]-adenosine, selecting said transformed embryonic callus, forming a somatic embryo from said transformed embryogenic callus and regenerating a transformed *Coffea arabica* from said somatic embryo.

2. A method as claimed in claim 1, wherein said vector is a binary vector pIG121-Hm, containing a β-glucuronidase gene, a hygromycin phosphotransferase gene and a neomycin phosphotransferase II gene.

3. A method as claimed in claim 1, wherein said vector is a binary vector pSMBuba, containing a phosphinothricin acetyl transferase gene and a hygromycin phosphotransferase gene.

4. A transgenic *Coffea arabica* plant produced by the method of claim 1, wherein said vector is a binary vector pIG121 -Hm, containing a β-glucuronidase gene, a hygromycin phosphotransferase gene and a neomycin phosphotransferase II gene.

5. A transgenic *Coffea arabica* plant produced by the method of claim 1, wherein said vector is a binary vector of pSMBuba, containing a phosphinothricin acetyl transferase gene and a hygromycin phosphotransferase gene.

* * * * *